United States Patent
Hsieh et al.

(10) Patent No.: US 9,738,937 B1
(45) Date of Patent: Aug. 22, 2017

(54) IDENTIFYING CANDIDATE CELLS USING IMAGE ANALYSIS

(71) Applicant: Cellmax, Ltd., Grand Cayman (KY)

(72) Inventors: Huangpin B. Hsieh, Palo Alto, CA (US); XiaoMing Wang, Dublin, CA (US)

(73) Assignee: Cellmax, Ltd., Grand Cayman (KY)

( * ) Notice: Subject to any disclaimer, the term of this patent is extended or adjusted under 35 U.S.C. 154(b) by 0 days.

(21) Appl. No.: 15/476,848

(22) Filed: Mar. 31, 2017

(51) Int. Cl.
- G06K 9/00 (2006.01)
- C12Q 1/68 (2006.01)
- G01N 15/14 (2006.01)
- G01N 33/574 (2006.01)
- G02B 21/00 (2006.01)
- G01N 33/50 (2006.01)

(52) U.S. Cl.
CPC ....... *C12Q 1/6886* (2013.01); *G01N 15/1475* (2013.01); *G01N 33/57492* (2013.01); *G02B 21/002* (2013.01); *C12Q 1/6883* (2013.01); *G01N 15/1468* (2013.01); *G01N 33/5094* (2013.01); *G01N 33/574* (2013.01); *G01N 33/57484* (2013.01); *G01N 2015/1472* (2013.01)

(58) Field of Classification Search
None
See application file for complete search history.

(56) References Cited

U.S. PATENT DOCUMENTS

| | | | | |
|---|---|---|---|---|
| 6,993,167 B1* | 1/2006 | Skladnev | ............... | A61B 5/444 382/128 |
| 7,308,139 B2* | 12/2007 | Wentland | ................. | G01V 1/34 382/109 |
| 8,600,143 B1* | 12/2013 | Kulkarni | ............ | G06K 9/00147 382/133 |
| 2003/0059093 A1* | 3/2003 | Rosania | ............. | G06K 9/00127 382/128 |
| 2003/0091221 A1* | 5/2003 | Marcelpoil | ............ | G01N 21/27 382/128 |
| 2006/0245631 A1* | 11/2006 | Levenson | ............ | G06K 9/6247 382/133 |
| 2012/0314926 A1* | 12/2012 | Ghosh | ..................... | G06T 7/136 382/131 |
| 2013/0011029 A1* | 1/2013 | Ron | ......................... | G06T 7/12 382/128 |
| 2014/0120537 A1 | 5/2014 | Chang et al. | | |
| 2014/0255976 A1 | 9/2014 | Chang et al. | | |

(Continued)

FOREIGN PATENT DOCUMENTS

WO WO 2013/003624 1/2013
WO WO 2015/153816 10/2015

*Primary Examiner* — Iman K Kholdebarin
(74) *Attorney, Agent, or Firm* — Fish & Richardson P.C.

(57) ABSTRACT

A method for identifying and enumerating candidate target cells within a biological fluid specimen is described. The method includes obtaining a biological fluid specimen, preparing the biological fluid specimen by staining cell features in the biological fluid specimen, capturing a digital image having a plurality of color channels of the biological fluid specimen, and applying image analysis to the digital image. A computer program product for identifying candidate target cells within a biological fluid specimen is also described. The computer program comprises instructions to cause a processor to carry out the image analysis.

22 Claims, 8 Drawing Sheets

(56) References Cited

U.S. PATENT DOCUMENTS

2015/0235362 A1\* 8/2015 Ghosh .................. G06T 7/0012
                                                        382/128
2016/0059234 A1\* 3/2016 Chang ............... B01L 3/502753
                                                        435/309.1

\* cited by examiner

IDENTIFYING CANDIDATE CELLS USING IMAGE ANALYSIS

TECHNICAL FIELD

The present disclosure relates to identifying candidate cells, e.g., circulating tumor cells, in an image of a sample.

BACKGROUND

Circulating tumor cells (CTCs) are cancerous cells, often of epithelial origin, that have detached from a primary tumor and entered the vasculature or lymphatic system. When CTCs invade the circulation, these malignant cells gain access to other organs. After shedding from a solid mass, CTCs may come to rest against a vessel wall and extravasate into surrounding tissue. Angiogenesis helps establish a new tumor at a site distant from the original mass. CTCs thus represent seeds for the growth of additional tumors (metastases).

It is understood that the number of CTCs in peripheral blood is associated with decreased progression-free survival and decreased overall survival in patients with metastatic disease, including breast, colorectal and prostate cancers. CTC detection and enumeration from blood or other bodily fluid samples can be used to evaluate tumor prognosis and assist in the management of cancer patients.

Tumors shed many cells. It is estimated that 1 million CTCs enter peripheral blood per gram of tumor tissue. Within 24 hours, however, only 0.1% remain viable. Viable CTCs are considered "rare" cells because they have been observed in the peripheral blood of cancer patients at very low concentrations, such as one CTC among $10^6$-$10^7$ leukocytes (Sakurai et al., 2016). They are also present against a high background of hematopoietic cells and thus their frequency is on the order of 1-10 CTCs per 1 mL of whole blood in patients with metastatic disease (Miller et al., 2010). CTCs are therefore difficult to detect and enumerate accurately.

Biological staining enhances microscopic image analysis. Certain dyes are used to highlight biological cell features and structures. CTCs have distinguishing histological features visible under a microscope when particular stains are applied.

SUMMARY

In one aspect, a method for identifying candidate target cells within a biological fluid specimen includes obtaining a biological fluid specimen, preparing the biological fluid specimen by staining cell nuclei in the biological fluid specimen, capturing a digital image having a plurality of color channels of the biological fluid specimen, and applying image analysis to the digital image.

In another aspect, a computer program product for identifying candidate target cells within a biological fluid specimen is tangibly embodied in a computer readable medium. The computer program comprises instructions to cause a processor to carry out the image analysis.

In another aspect, a method for enumerating a target cell population within a biological fluid specimen includes the method of identifying candidate target cells, followed by classifying a candidate as a target cell or a non-target element based on a portion of the image corresponding to a remaining identified spatially overlapping first connected region and second connected region, and counting any candidate classified as a target cell, to generate a count value.

In another aspect, a method for determining likelihood of cancer in a human subject includes comparing the count value with a statistically determined count of circulating epithelial cells from a group of tumor-free patient controls, and assigning a likelihood of cancer occurrence when the total count exceeds a pre-determined value based on statistical averages of circulating epithelial cell counts from healthy subjects compared with statistical averages of circulating epithelial cell counts from cancer patients.

Preparing the biological fluid specimen includes staining cell nuclei in the biological fluid specimen with a first bio-conjugated dye having a first color and configured to bind nucleic acids in the cell nuclei of the target cells and staining cytoskeletal cell features in the biological fluid specimen with a second bio-conjugated dye having a second color and configured to bind to cytoskeletal cell features of the target cells and staining white blood cells in the biological fluid specimen with a third bio-conjugated dye having a third color and configured to bind to human leukocyte antigens in the biological fluid specimen.

Applying image analysis includes receiving the digital image, identifying first connected regions of pixels of a minimum first intensity in a first channel of the plurality of color channels, identifying second connected regions of pixels of a minimum second intensity in a second channel of the plurality of color channels, determining first connected regions and second connected regions that spatially overlap, determining an aspect ratio of the spatially overlapping first connected regions and second connected regions based on a color channel of the plurality of color channels, identifying first connected regions and second connected regions that spatially overlap and for which the aspect ratio meets an aspect ratio threshold, determining a second connected region and a third connected region that spatially overlap, determining an intensity ratio of the spatially overlapping second connected region and third connected region based on two color channels of the plurality of color channels, eliminating as a candidate a spatially overlapping first connected region and second connected region corresponding to a spatially overlapping second connected region and third connected region for which the intensity ratio does not meet an intensity ratio threshold, and providing a portion of the image corresponding to a remaining identified spatially overlapping first connected region and second connected region to a classifier as candidates for classification.

Implementations may include one or more of the following features.

The first color may be blue, the second color may be red or orange, and the third color may be green.

The first stain or bio-conjugated dye may include DAPI (4',6-diamidino-2-phenylindol). The second stain or bio-conjugated dye may include a red or orange fluorescent dye conjugated to an anti-cytokeratin (CK) antibody. The third stain or bio-conjugated dye may include a green fluorescent dye conjugated to an anti-CD45 antibody, or a combination of a first antibody, anti-CD45, and a second antibody pre-conjugated to a green fluorescent dye and targeting CD45.

The second stain or bio-conjugated dye may include a red or orange fluorescent dye conjugated to an anti-cytokeratin (CK) antibody, or a combination of a first antibody, anti-CK, and a second antibody pre-conjugated to a red or orange fluorescent dye and targeting CK.

In a particular implementation, by way of example, the second stain or bio-conjugated dye may include an ALEXA568®-conjugated anti-cytokeratin antibody, and the third stain or bio-conjugated dye may include an anti-CD45-ALEXA488® antibody or a combination of a first antibody, anti-CD45, and a second antibody pre-conjugated to ALEXA488® and targeting CD45.

The second stain or bio-conjugated may include an ALEXA568®-conjugated anti-cytokeratin (CK) that includes monoclonal antibodies that are conjugated to ALEXA568® or a combination of a first antibody, anti-CK, and a second antibody pre-conjugated to ALEXA568® and targeting CK.

Identifying the first connected regions may include identifying first connected regions that have a minimum first size, and identifying the second connected regions may include comprise identifying second connected regions that have a minimum second size. Identifying the first connected regions may include identifying first connected regions that have a maximum first size, and identifying the second connected regions may include identifying second connected regions that have a maximum second size. Identifying the first connected regions and identifying the second connected regions comprises a maximally stable extremal regions (MSER) algorithm.

Identifying the first connected regions may include dividing the digital image into a plurality of portions, searching each portion for a potential first connected region, and identifying a new portion of the digital image centered on a potential first connected region found from the search. Determining first connected regions and second connected regions that spatially overlap may include determining whether a boundary of a second connected region fits inside or overlies a boundary of the first connected region.

A combination of the first connected region and the second connected region may be determined. Determining the aspect ratio may include finding a major axis that extends between two points that are farthest apart on a boundary of the combination, finding a minor axis that extends perpendicular to the major axis and between two points that are farthest apart on the boundary on opposites sides of the major axis, and calculating a ratio of the minor axis to the major axis. The aspect ratio threshold may be 0.4 or less.

A boundary box around the combination may be determined, a first number of pixels within a boundary of the combination and a second number of pixels in an extent may be determined, a ratio of the first number of pixels to the second number of pixels may be determined, and the ratio may be compared to an extent threshold. The extent threshold may be between 0.4 and 0.85. The combination may be a union of the first connected region and the second connected region.

Determining the intensity ratio may include determining a first average intensity of the second connected region, determining a second average intensity of the third connected region, and determining a ratio of the first average intensity to the second average intensity. The spatially overlapping second connected region and third connected region may be eliminated if the ratio is below the threshold. The spatially overlapping second connected region and third connected region may be eliminated if (I2/I3)<1, where I2 is the first average intensity and I3 is the second average intensity.

Advantages may include one or more of the following.

Areas within a sample region that are likely to contain candidate cells of interest can be located automatically. These areas can be flagged for further evaluation. This can significantly reduce the number of sample areas that would otherwise need to be reviewed by a human operator. Such an automated imaging process for CTC detection and enumeration can aid in predicting disease progression and overall survival during therapy, and could allow for serial monitoring of patient prognosis, leading to more informed patient care choices.

BRIEF DESCRIPTION OF DRAWINGS

Like reference symbols in the various drawings indicate like elements.

DETAILED DESCRIPTION

Sampling of solid tumors is a routine procedure in cancer diagnostics. Next-generation sequencing now enables sensitive, rapid and low-cost detection and analysis of tumor DNA from cancer cells or its constituent DNA that have strayed beyond their original tissues into fluid components between cells, such as, for example, interstitial fluid, lymph, blood, saliva, cerebral spinal fluid, synovia, urine, feces and other secretions. Cancer cell debris sampled away from a primary tumor can serve as a marker to monitor disease progression and potentially assist in cancer diagnosis before symptoms appear.

The process of identifying CTCs on a sample slide begins with narrowing the regions of the sample slide where candidate CTCs exist for further manual review. CTCs typically measure between 8 µm to 25 µm and a typical sample area is between roughly 50 mm$^2$ to 1200 mm$^2$. Confirmation of "positive events" by visual inspection of tumor cell morphology or other cell characteristics is necessary. Given the large sample area from which CTCs must be located, it is difficult and laborious to manually identify candidates over an entire slide region, and inefficient for a human operator to evaluate imaged slide samples. Some positive events can also be missed, especially when candidates in the images are present in low frequencies. Thus, detection and quantification of CTCs is very challenging. The digital image analysis described herein in conjunction with a high resolution microscope can be used to efficiently identify candidate CTCs of interest.

Figure 1:
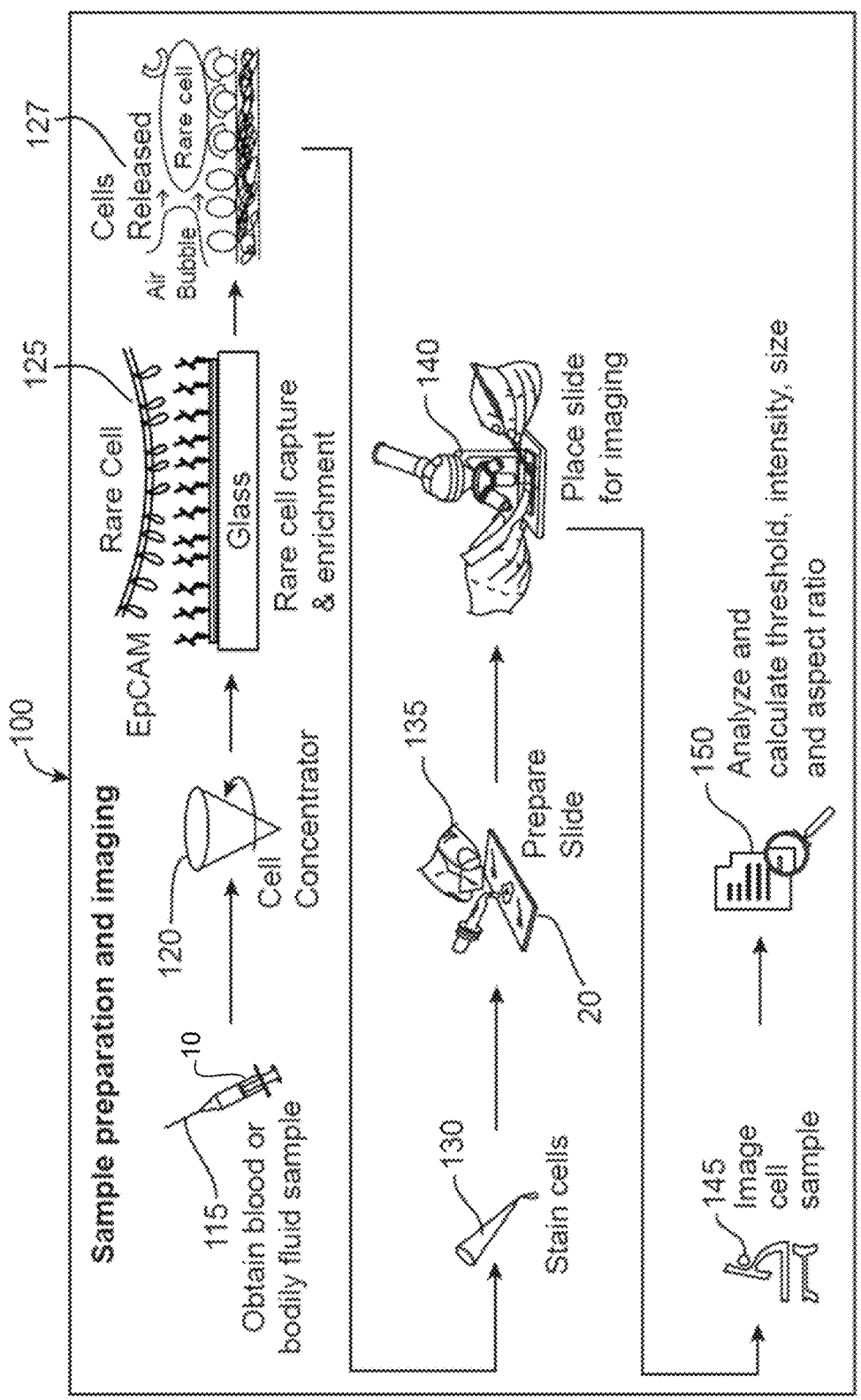
FIG. 1 is a schematic illustration of a process of identifying CTCs.

FIG. 1 is a schematic illustration of an example of a process 100 of identifying CTCs. Referring to FIG. 1, a sample 10 of a biological fluid, e.g., a bodily fluid such as blood, lymph, cerebral spinal fluid, saliva, synovia, urine, feces or another secretion, is received from a clinical site (step 115). For example, a doctor may wish to have a patient tested, e.g., to detect a cancer before symptoms appear, diagnose a particular cancer, monitor the progression of a cancer or characterize the DNA of cancer cells in order to select appropriate treatment options.

The patient's blood or other bodily fluid sample can be collected at the doctor's office or at a medical clinic, and the sample sent to the operator of the system 200. In other implementations, the sample may be collected at the site of the system 200.

The sample can also be subjected to an enrichment process (step 120 through step 125). Enrichment of a sample for cancer cells is especially useful when blood samples are being evaluated.

Several CTC enrichment technologies exist to reduce the total number of cells that must be analyzed. Examples include antibody-functionalized microfluidic devices, cell-size based filtration, passive cell sorting, and immunomagnetic isolation. Other methods, compositions and systems for isolating cancer cells of interest include those described in PCT/US2015/023956, which claims the benefit of U.S. Provisional Application No. 61/973,348, filed Apr. 1, 2014 and U.S. Provisional Application No. 61/975,699, filed Apr. 4, 2014, as well as U.S. application Ser. No. 14/065,265, which published as U.S. 2014/0120537, which claims the benefit of U.S. Provisional Application No. 61/719,491, filed Oct. 29, 2012, as well as U.S. application Ser. No. 14/836,390, which published as U.S. 2016/0059234, and which claims the benefit of U.S. Provisional Application No. 62/042,079, filed Aug. 26, 2014, all expressly incorporated herein by reference.

For example, as described in the above-cited references, target CTCs can be flowed through a microfluidic channel comprising a surface, such as glass (FIG. 1, step 125). The surface can comprise a binding moiety, to which the CTCs of interest attach (EpCAM schematic binding illustrated in FIG. 1, step 125). The surface can comprise a non-fouling composition, such as a lipid composition, a bioactive composition and/or functional groups, which lessens the binding of non-specific particles. The purity of the CTCs of interest is therefore enriched by reducing the binding of non-specific particles. Once the CTCs of interest are captured on this surface, which can comprise a lipid bi-layer, for example, they can be washed and stained with a panel of antibodies using a gentle sweeping force to maintain cell integrity (FIG. 1, step 127 through step 130). The force may be, for example, a shear of air bubbles, a shear of air foams, a shear of emulsive fluid, ultrasonic vibrations or an oil phase. In one specific example, a foam composition comprising air bubbles is flowed over the surface to remove bound cells and/or non-fouling compositions (FIG. 1, step 127). In another example, as described in PCT/US2012/044701 and U.S. application Ser. No. 14/128,354, which published as U.S. 2014/0255976, and which claims the benefit of U.S. Provisional Application No. 61/502,844, filed Jun. 29, 2011 and U.S. Provisional Application No. 61/606,220, filed Mar. 2, 2012, all expressly incorporated herein by reference, a "releasable" composition acts to lubricate the surface so that only low flow shear stress is required to remove or release non-specific cells or blood components from the surface coating.

By way of example, target CTCs are released for imaging and analysis by flowing a foam across the microfluidic surface, which enhances efficiency and viability of the cells, as described in PCT/US2015/023956, which claims the benefit of U.S. Provisional Application No. 61/973,348, filed Apr. 1, 2014 and U.S. Provisional Application No. 61/975,699, filed Apr. 4, 2014, all expressly incorporated herein by reference.

In more general, less sophisticated examples, peripheral blood can be enriched for nucleated cells by using RBC lysis buffer in conjunction with positive immunomagnetic selection. Erythrocytes can be lysed by adding RBC lysis buffer, mixing by inversion, and incubating.

Another example of an enrichment process uses a highly overexpressed cell surface biomarker with high specificity and sensitivity for CTCs, such as the epithelial cell adhesion molecule (EpCAM). The CELLSEARCH SYSTEM® (Veridex) utilizes anti-EpCAM antibody-coated magnetic nanoparticles to capture and enrich CTCs, followed by cytokeratin immunostaining. The ADNATEST® (AdnaGen AG, Germany), another commercially available system for CTC detection, adopts a similar immunomagnetic approach by using anti-EpCAM and Mucin 1 (MUC1) conjugated magnetic beads. More recently, "CTC chips" based on anti-EpCAM antibody-coated microfluidics chip were developed for CTC detection and enrichment (Nagrath et al., *Nature* 2007, 450:1235-9). The patent applications referenced above address non-specific binding of blood cells with anti-EpCAM antibody.

Next a staining process (step 130) is applied to the sample. In some cases, immunological methods, whereby antibodies directed to characteristic cellular constituents, can be used to stain cells of interest. Cell staining can be performed using monoclonal antibodies, which recognize specific cell types and features within a population of cells. The antibodies may be directly labeled with a fluorescent compound or indirectly labeled using, for example, a fluorescent labeled second antibody which recognizes the first antibody. A panel of antibodies may be used to analyze a cell population in a multi-marker imaging approach. For example, different antibodies may be labeled with different colors and subsequently imaged. In some instances, a multi-marker imaging approach may increase the sensitivity of detection of CTCs.

Detecting and enumerating CTCs in bodily fluid samples is based on the premise that generally cells of epithelial origin are defined as nucleic acid$^+$, CD45$^-$ and cytokeratin$^+$ (CK). Immunocytochemical staining for any number of different cytokeratins (CKs) can be performed with fluorescently-conjugated antibodies or antibody fragments. Cells may be fixed in ice-cold methanol, rinsed in PBS, and incubated with an anti-cytokeratin antiserum or a monoclonal antibody or antibody fragment directed against pan-cytokeratin (inclusive of all types of cytokeratins), class I or II cytokeratins, or anti-individual cytokeratin isotypes (e.g., cytokeratin 1 to cytokeratin 20), or a combination of any number of cytokeratin isotypes.

Cells may also be incubated with another first (primary) antibody such as CD45 against WBCs and/or a second antibody against the primary CD45. The sample can then be counterstained with 0.5 µg/ml DAPI in PBS at room temperature for 10 min, and mounted in glycerol-gelatin.

Specimens may be fixed in neutral, buffered formaldehyde and then permeabilized (step 135). Alternatively, slides can be dried and cover-slipped with a cellulose triacetate film or mesh, anti-fade. In step 135, the total number of cells applied per slide can be in the range of 100 to $1.5 \times 10^6$. An adhesive area on the slides may consist of one to three separate circles for image analysis totaling 100 to 530 mm$^2$.

The staining process includes at least two stains of different colors: cell nuclei in the biological fluid specimen are stained a first color, and cytoskeletal cell features in the biological fluid are stained a second color. Optionally, white blood cells or other non-target cells in the biological fluid can be stained a third color. One or both of these stains is configured to bind preferentially to the cells of interest, e.g., using an antibody that specifically recognizes and binds to cell-surface markers or cytokeratin, for example. In some implementations, cell nuclei can be stained with a first bio-conjugated dye that is configured to provide a first color when imaged and to bind nucleic acids in the cell nuclei of the target cells. Cytoskeletal cell features can be stained with a second bio-conjugated dye configured to provide a second color when imaged and configured to bind to cytoskeletal cell features of the target cells. In particular, the second stain can include an antibody or antibody fragment that binds to cytoskeletal cell features, such as cytokeratin though direct immunofluorescence. The antibody may be conjugated to a fluorescent protein, a second antibody, or other fluorescent chemical compound that can re-emit light upon excitation with light. In this way, two antibodies may be used to achieve an amplifying effect through indirect immunofluorescence. In recognizing cytoskeletal cell features such as cytokeratin, the second stain may mark any number of cells having a cytoskeleton. This includes and is not limited to epithelial cells, endothelial cells, endothelial progenitor cells, 'cancer stem cells' and disseminated tumor cells, for example. White blood cells can be stained with a third bio-conjugated dye, such as Green Fluorescent Protein (GFP), configured to provide a third color when imaged and configured to bind to human leukocyte antigens. Indirect immunofluorescence can also be used with the third stain or bio-conjugated dye to amplify the signal.

Figure 2:
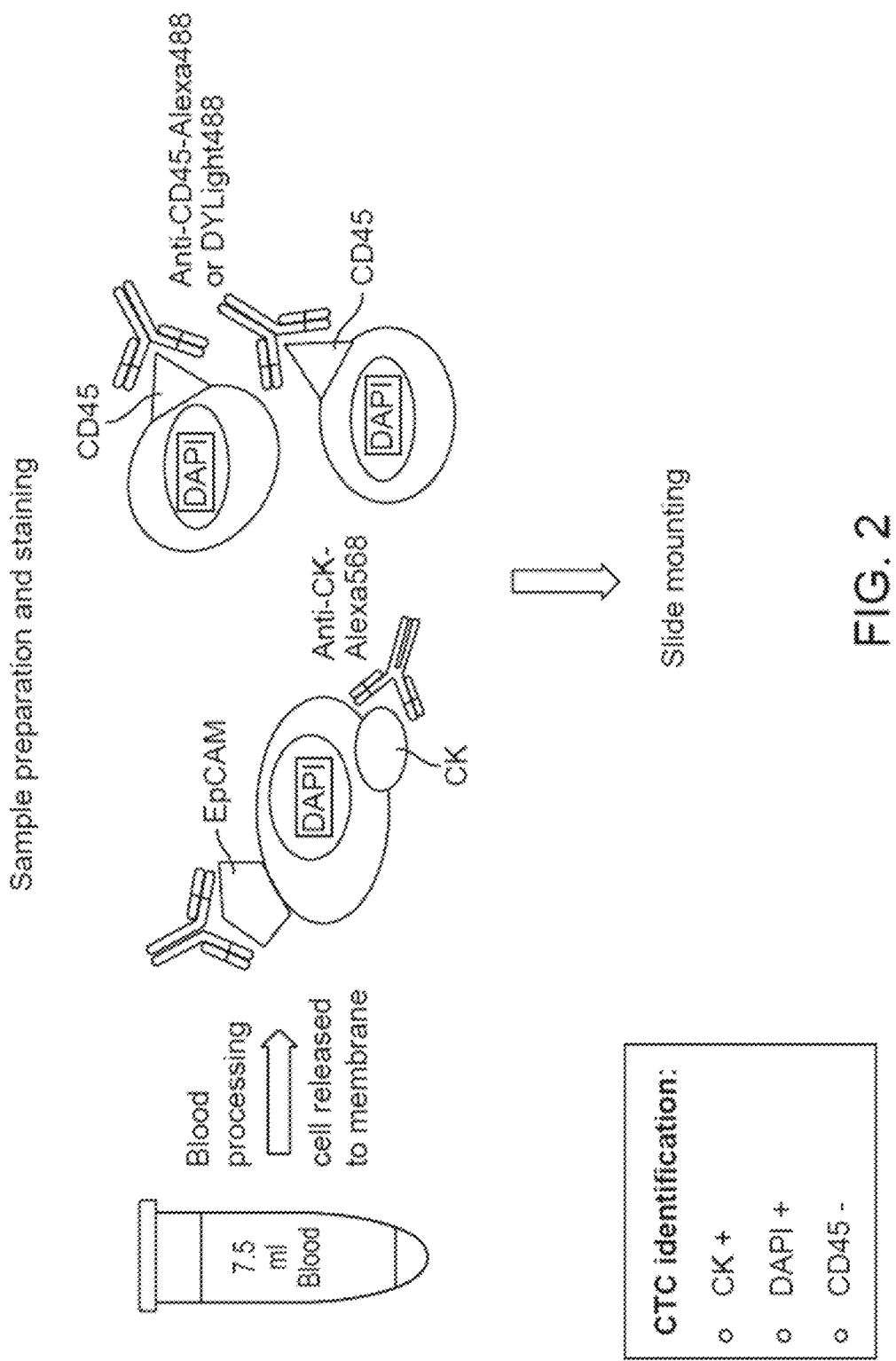
FIG. 2 is a schematic diagram illustrating a staining process.

Referring now to FIG. 2, in one particular implementation, the first stain can include a nuclear stain such as DAPI (4',6-diamidino-2-phenylindol). A CTC should stain positive for a nucleic acid dye, such as DAPI, showing that the nucleus is contained within the cytoplasm and smaller than the cytoplasm. The presence of a nucleus indicates that the cell is not a red blood cell, which is a-nuclear.

The second stain can include one or more dye-conjugated anti-cytokeratins (CKs). These may comprise monoclonal antibodies specific for cytokeratin that are conjugated to allophycocyanin (APC), phycoerythrin (PE) or any number of commercially available fluorescent molecules such as ALEXA FLUOR® or DYLIGHT® dyes. In a particular example shown in FIG. 2, the second stain includes an antibody that is specific for cytokeratin (CK) (small oval) and conjugated to ALEXA568®, a small molecular organic dye with fluorescent red emission spectra, thus capable of marking and differentiating epithelial cells. A CTC should stain positive for ALEXA568®-conjugated anti-cytokeratin, be round, oval or polygonal with an intact membrane and at least about 4 µm in size.

The third stain can include anti-CD45, a monoclonal antibody specific for CD45, an antigen present on the surface of leukocytes, conjugated to Green Fluorescent Protein (GFP), for example, or any number of commercially available organic dyes such as ALEXA488® or DYLIGHT488®, with fluorescent green emission spectra, by way of illustration. A CTC should not stain positive for CD45, as this stain recognizes an antigen present on leukocytes, and CTCs cannot be white blood cells. While particular dyes are discussed, other similar dyes known in the art are also contemplated.

The first color can be red or orange, the second color can be blue, and the third color can be green, although other color combinations are possible. The dyes can be fluorescent dyes that luminesce under light, e.g., UV light or visible light or infrared light, applied during the imaging process. Alternatively, the dyes can be absorptive dyes.

Once the stains are applied, the sample is transferred to an observation slide 20 (FIG. 1, step 135). For example, the slide 20 can include a filter 22 (see FIG. 1 and FIG. 3), such as a porous membrane or mesh, and the sample can be dispensed onto the filter so that the filter captures candidate cells, e.g., candidate CTCs, while permitting other fluid to flow through the filter. The filter might also capture other cells, e.g., white blood cells or other non-target cells. The filter 22 can be mounted on top of the observation slide 20. The observation slide 20 can be glass, plexiglass, or similar suitable material known in the art. The filter 22 can be about 5~25 mm in diameter with an average pore size (e.g., spacing of the mesh) up to 10 µm, e.g., from 1 to 3 µm or from 2 to 5 µm. The average pore size can be less than 2 µm. The filter 22 can be a plastic, e.g., polycarbonate.

The sample can now be analyzed (FIG. 1, steps 140-150). In particular, candidate cells, e.g., candidate CTCs, can be identified, without requiring input from a technician, using the system 200 (see FIG. 3) discussed below. The slide 20 can be placed for imaging (step 140), the sample can be imaged (step 145), and the images analyzed to identify candidate cells (step 150).

Figure 3:
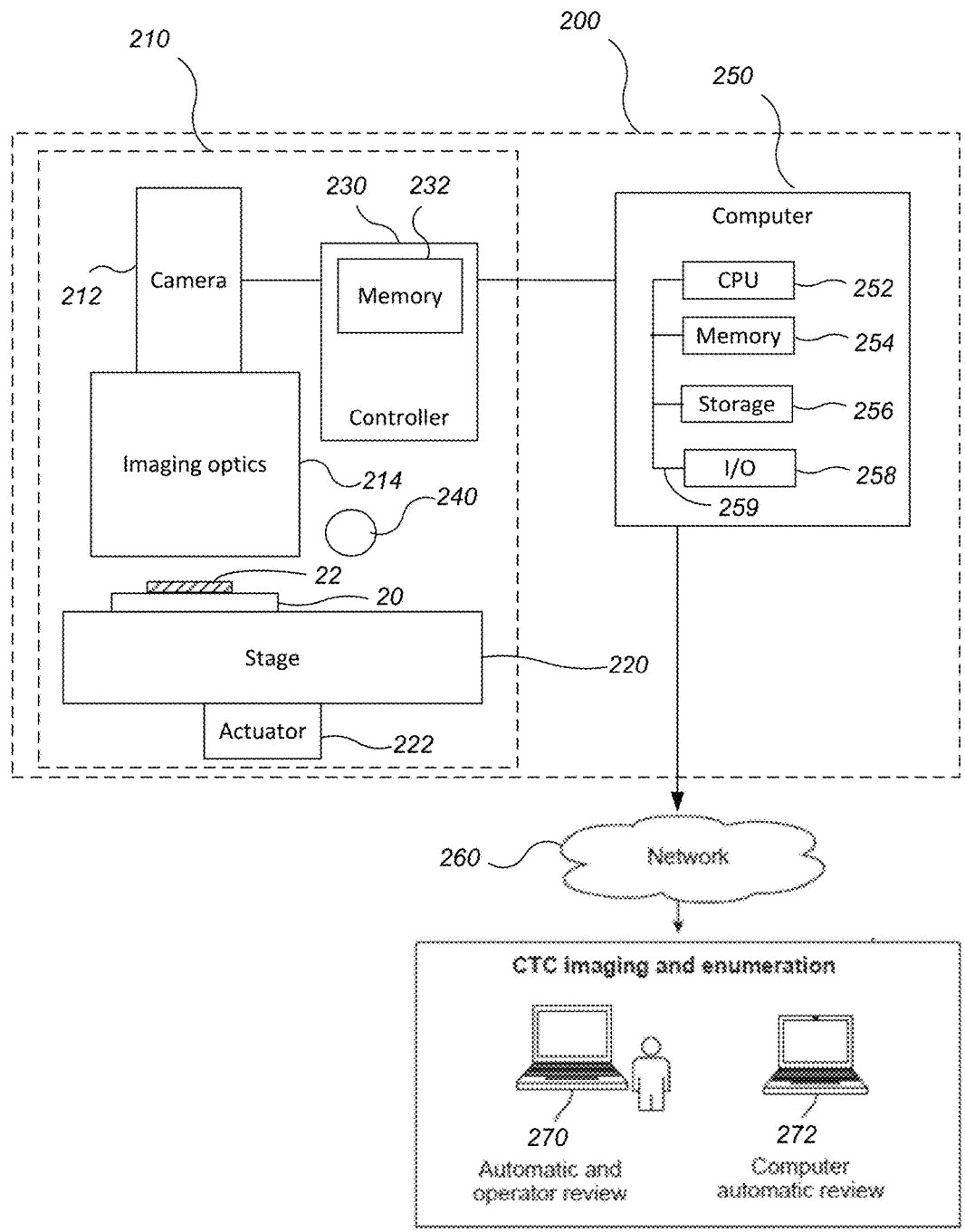
FIG. 3 is a schematic diagram of a system for identifying CTCs.

FIG. 3 is a schematic diagram of a system for identifying CTCs. Referring to FIG. 3, the system 200 includes an imaging microscope 210 and at least one computer 250 that can be configured to control the capture mechanism of the microscope, control the relative motion between the stage and microscope, e.g., in X, Y and/or Z directions, and/or control activation of the lights source and/or movement of the optic filters to excite and capture fluorescent lights at different wavelengths. The computer 250 is also configured to analyze images from the microscope 210 and identify candidate cells, e.g., candidate CTCs, in the sample.

The imaging microscope 210 includes a digital camera 212 and optical components 214, e.g., lenses and the like, to focus the camera 212 on a spot on a slide held on a stage 220. The stage can be undergo motorized movement in the X, Y and/or Z directions as controlled by the computer 250. The digital images captured by the microscope 210 have at least two color channels, e.g., three channels, e.g., a red channel, a green channel and a blue channel. Each color channel can correspond to the color generated by one of the dyes, although an exact wavelength correspondence is not required. The resolution and magnification of the imaging microscope can be selected such that an individual pixel corresponds to 0.3 to 1.3 µm on a side, e.g., about 0.648 µm$^2$. In one example, the imaging microscope 210 can use a 10× objective lens and a digital camera configured to generate a digital image of 1392×1040 pixels with three color channels and 12 bits per channel per pixel.

The camera can be coupled to or include a memory 232 to store digital images from the camera 212. The memory 232 can be part of a controller 230, e.g., a general purpose computer running an application, for controlling the microscope 210.

The stage 220 can be supported by an actuator 222, e.g., a three-axis actuator configured to move the stage 220 along two perpendicular horizontal axes that are parallel to the plane in which the slide 20 is held and a vertical axis that is perpendicular to the plane. Alternatively, the actuator 222 could move the camera 212 and optical components 214 while the stage 220 remains fixed in place.

The actuator 214 can be coupled to the controller 230. The controller 230 can be configured to create relative motion between the stage 220 and camera 212 so as to automatically scan the area imaged by the microscope 210 across the slide 20 and to control the timing of capture of images by the camera 212 so as to generate an array of digital images that cover the area in which the sample is disposed, e.g., the filter area 22. The controller 230 can be configured to permit an operator to configure the microscope 210 or adjusting scanning parameters.

The imaging microscope 210 can also include a light source 240. Assuming that the stains include fluorescent dyes, then the light source 240 generates light at a wavelength appropriate to cause the dyes to fluoresce, e.g., UV to visible to infrared light. Thus, the imaging microscope 210 can produce digital images of the stains, e.g., the nuclear, cytokeratin, and CD45 stains. Assuming fluorescent dyes are used and that the filter 22 is composed of a material that does not fluoresce under the light from source 240, the filter should not show up in the digital image. Alternatively, if passive dyes are used, the light source 240 can generate white light.

The digital images are then transferred to the computer 250 for storage and analysis. The digital images can be stored and/or transmitted in a lossless format such as tiff. For example, the computer 250 can be coupled to the microscope 210, e.g., by a serial bus connection such as a USB connection, or a network such as an Ethernet or the Internet, and the computer 250 can be configured to automatically retrieve the digital images from the memory 232. Alternatively, the computer 250 itself could provide the controller 230; in this case the memory 232 could be part of the computer 250. Alternatively, the memory 232 could be a portable device, e.g., a Flash drive, which can be physically removed by the operator from the microscope 210 and inserted in the computer 250, which may be a distinct computer separate from the computer that operates the microscope.

In any case, the computer 250 is configured to receive the digital images and analyze them to identify candidate cells, e.g., candidate CTCs and/or white blood cells (WBCs). In general, digital images of the candidate cells identified by the computer 250 would need to be reviewed by a technician to confirm that each candidate is, in fact, a cell of interest, e.g., a CTC. However, by automatically rejecting a large percentage of any extraneous objects from the digital image, the number of candidates for a technician to evaluate can be significantly reduced, thus increasing efficiency and reducing time needed to generate a test result.

Figure 4:
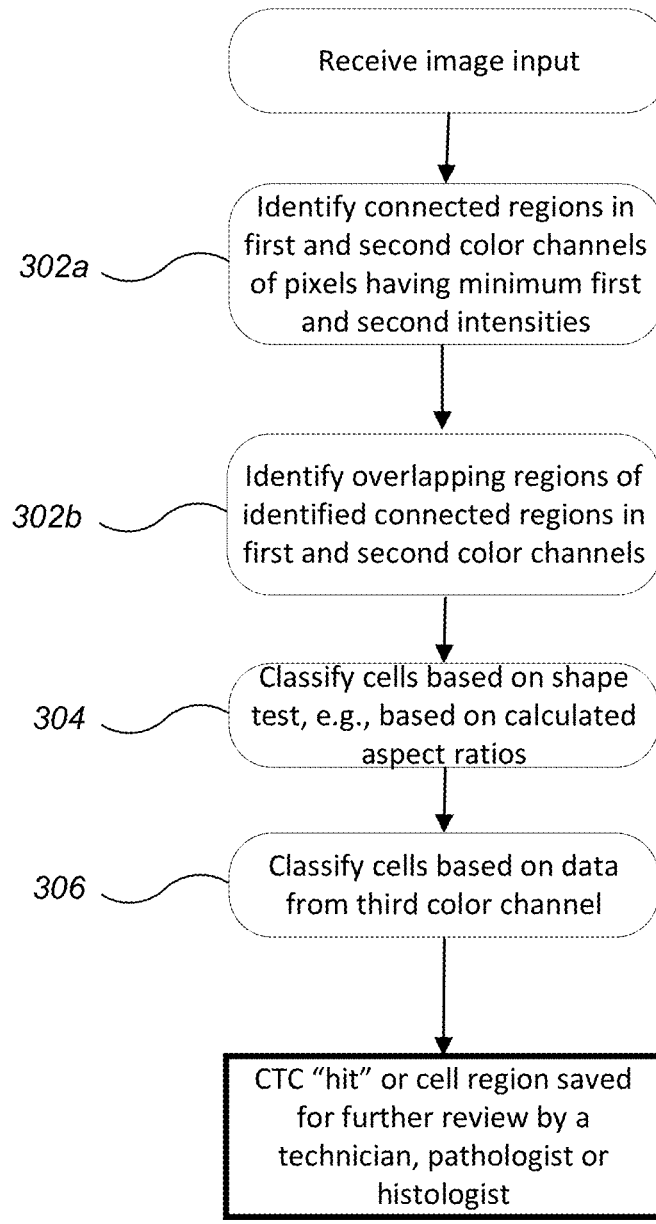
FIG. 4 is a flow chart of a computer-implemented process of identifying candidate cells in a digital image.

Referring to FIG. 4, the computer-implemented process to identify candidate cells includes three main steps. First, the computer 250 identifies overlapping "blobs" (i.e., connected regions of pixels having a minimum intensity) in two color channels of the digital image (see steps 302a and 302b). The first color channel can correspond to the first color, e.g., to the staining of the nucleic acids in the cell nuclei of the target cells, and the second color channel can correspond to the color of the second dye, e.g., to the staining of the cytoskeletal cell features of the target cells. Second, the computer 250 subjects a shape generated from a combination of overlapping blobs to one or more shape tests (step 304). This can exclude image artefacts as well as some types of cells. Third, the computer 250 can exclude shapes based on an evaluation of a third color channel (step 306). The third color channel can correspond to the third color, e.g., to the staining of white blood cells. This can exclude white-blood cells. If prior processes, e.g., enrichment, are sufficiently effective at removing white-blood cells from the sample, then this third step could be optional. Each of these steps will be discussed in greater detail below.

Returning to FIG. 3, as the computer 250 identifies the candidate cells, it stores identifying information for each candidate cell. For example, the computer 250 could insert a tag, e.g., a bookmark, into the digital image, could store the coordinate of the candidate cell within the digital image in a database, or could clip a portion of the digital image corresponding to the candidate cell and save that portion in a separate file or database.

The identifying information, and the digital image if needed, can be forwarded to a classifier for a post-process or off-line inspection to determine whether each candidate should be classified as a target cell. The identification of candidate cells can also be performed by the classifier.

The classifier can be a human technician who will inspect the digital image. For example, the computer 250 can be coupled to a computer 270 by a network 260, e.g., a local area network (LAN) or the Internet.

A technician can use the computer 270 to review the portion of the digital image corresponding to each candidate cell, e.g., views the portion of the digital image, and determines whether the candidate is, in fact, a target cell, e.g., a CTC. For example, the computer 270 may be configured to automatically receive the identifying information, determine a portion of the digital image based on the identifying information, and display in a controlled sequence the determined portion on a display of the computer 270 to the technician. For example, the computer 270 can receive the coordinates of the candidate cell, select a portion of the digital image centered at the coordinates, and then automatically display the selected portion. This can reduce the need for the technician to search through the digital image for the candidates. In another implementation, the technician may receive a list of candidates, with each element in the list linked to a portion of the digital image. Selection of an element from the list by the user can cause the computer to present the corresponding portion of the digital image to the technician.

Alternatively, if in the future it becomes possible to entirely automate determination of whether candidate cells are target cells, this task could be performed by providing the proper instructions to a computer 272. In this case, the classifier is the computer 272. For example, the computer 250 can be coupled to a computer 272 by the network 260.

In some implementations, the computer 270 or 272 is configured to count the number of cells that are determined to be target cells, e.g., by the technician or automatically. This count can be used to generate a score, e.g., a total number of CTCs, a percentage, a ratio relative to a healthy individual, or the like. In other implementations, the score may be generated from a regression equation which include, in addition to CTC counts, other risk factors such as age, gender, body mass index, family cancer history, alcohol usage, physical activities or other life styles, to name a few. Eventually test results are returned to the entity, e.g., the doctor, who ordered the test. The test results could include the score, the portions of the digital image corresponding to the target cells, or both. Based on these test results, a doctor could, for example, determine the likelihood of cancer occurrence or recurrence by comparing the score with a statistically-determined score of circulating epithelial cells from a group of tumor-free patient controls. Based on this comparison, a doctor could assign a likelihood of cancer occurrence or recurrence when the total score obtained exceeds a pre-determined value based on statistical averages of circulating epithelial cell counts from healthy subjects.

The score can also serve to screen for undetected cancer in healthy individuals, diagnose cancer in patients with symptoms or detect a putative change in patient status. In one implementation, the score assists in determining an appropriate course of treatment for aggressive or indolent forms of cancer. In this regard, DNA within the CTCs sampled from the patient can be sequenced using next-generation sequencing technologies to identify cancer driver mutations. The mutations can be evaluated against panels of genetic markers that are understood to correlate with particular targeted therapies. Targeted therapies attack specific types of cancer cells with less harm to normal cells. One example is HERCEPTIN® (Genentech, USA), an antibody pharmaceutical, which targets the human epidermal growth factor receptor 2, HER2, which is over-expressed on the surface of cancerous ovarian and breast tissue.

The CTCs within a patient's sample can be subjected to other genetic tests. In the case of lung cancer, a blood draw to assess CTCs benefits patients that are too ill to provide a lung tumor biopsy. Based on a simple blood draw and CTC sequencing, genetic tests of the CTC DNA can reveal whether a patient has non-small cell lung cancer, which harbors epidermal growth factor receptor (EGFR) gene mutations. Knowing the genetic makeup of a tumor helps physicians decide whether a patient would benefit from regular chemotherapy or a targeted anti-cancer agent like TARCEVA®, which inhibits particular activated mutated forms of the EGF receptor.

By detecting, and enumerating CTCs, and further sequencing the DNA in CTCs, doctors can better understand a patient's particular cancer subtype. This can inform therapy choices and improve outcomes. In the case of breast cancer, for example, 70% of tumorous cells express an overabundance of hormone receptors, which bind estrogen or progesterone and stimulate cell growth. These tumors are best treated with hormonal therapy. Among other breast cancer subtypes, about 20%, have an overabundance of receptors that bind human epidermal growth factor 2 (HER2). These cells are best attacked with drugs like TYKERB® (Novartis, USA) and HERCEPTIN® (Genentech, USA), which target the HER2 receptor. Other breast cancer cells, roughly 10%, are "triple negative" meaning they do not have an overabundance of any of these receptors, and may instead harbor mutations in the BRCA tumor-suppressor genes. HERCEPTIN® (Genentech, USA) would not be appropriate treatment for these tumors, and treatment of patients without the benefit of information provided by the detection, quantification and sequencing of CTCs could result in suboptimal outcomes and potentially increased mortality.

Figure 5:
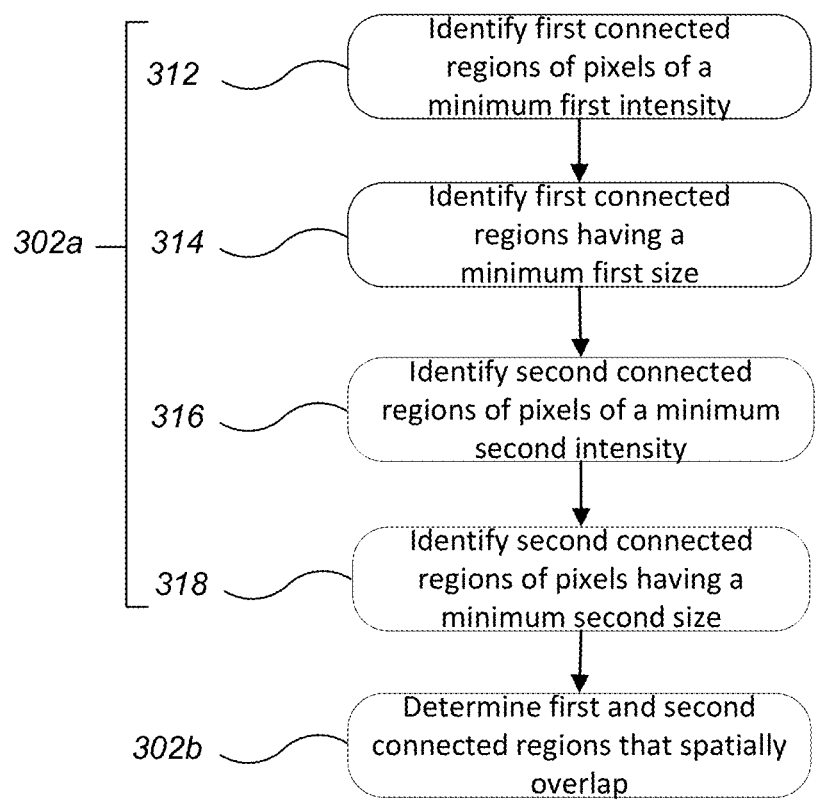
FIG. 5 is a flow chart of a computer-implemented process of identifying overlapping "blobs" in the digital image.

Turning to the process implemented by computer 250, FIG. 5 is a flow chart of a computer-implemented process of identifying overlapping "blobs" in the digital image. To identify each "blob," the computer identifies connected regions of pixels that have a minimum intensity. The connected regions are contiguous areas of adjacent pixels in the digital image. Each connected region can be subject to a size test, e.g., whether the region has a size, e.g., in total number of pixels, between an upper threshold and a lower threshold. The upper threshold and lower threshold can be predetermined based on the resolution of the image (i.e., number of pixels per micron) to correspond to physical sizes (e.g., in microns) that would correspond to CTCs.

In particular, to identify each "blob" in the first color channel, the computer identifies first connected regions of pixels of a minimum first intensity in the first color channel (step 312).

Whether the first connected region has a minimum first size is determined (step 314). For example, the total number of pixels in the first connected region can be calculated. If the first connected region has a total number of pixels less than a first lower threshold, e.g., fifty pixels, it will be eliminated as a candidate. Since a cell nucleus has a minimum size, if the first connected region is too small, this indicates that the "blob" in the first channel is not a cell nucleus and thus not a candidate.

In addition, whether the first connected region has a maximum first size can be determined. For example, if a first connected region has a total number of pixels greater than a first upper threshold, e.g., fifteen-hundred, e.g., one thousand pixels, it will be eliminated as a candidate. Since a cell nucleus has a maximum size, if the first connected region is too large, this indicates that the "blob" is not a cell nucleus and thus not a candidate.

A similar process can be performed for the second color channel. To identify each "blob" in the second color channel, the computer identifies second connected regions of pixels of a minimum second intensity in the second color channel (step 316).

Whether the second connected region has a minimum second size can be determined (step 318). For example, the total number of pixels in the second connected region can be calculated, e.g., by rasterizing through the image after the region has been determined and counting the pixels that are marked as being in the second connected region. If the second connected region has a total number of pixels less a second lower threshold, e.g., one-hundred pixels, it will be eliminated as a candidate. Since a cell has a minimum size, if the first connected region is too small, this indicates that the "blob" in the second color channel is not a cell and thus not a candidate.

In addition, whether the second connected region has a maximum second size can be determined. For example, if a second connected region has a total number of pixels greater than a second upper threshold, e.g., one thousand five hundred pixels, it will be eliminated as a candidate. Since a cell has a maximum size, if second connected region is too large, this indicates that the "blob" is not a cell and thus not a candidate.

Instead of comparing the number of pixels to a threshold number, the number of pixels could be divided by a resolution, e.g., number of pixels per unit area, and then compared to thresholds that represent sizes in units of area, e.g., in square microns.

One implementation of identifying connected regions of pixels that have a minimum intensity is to convert a gray-scale image into a binary image through thresholding (e.g., those pixels having lower than the minimum intensity are set to zero, those pixels having greater than the maximum intensity are set to one). The process examines pixels of the binary image, e.g., running from top to bottom and left to right in the digital image, determining whether the pixel is adjacent another pixel that has already been assigned to a blob. If the pixel is adjacent a pixel from an existing blob, the pixel can be assigned to the already identified blob. Otherwise a new blob data record will be created and stored (e.g., the pixel is assigned a new blob record). The minimum intensity can be selected through empirical research to be a value that distinguishes cells from noise, e.g., by an operator adjusting the minimum intensity in each color channel while a sample image is being displayed and determining by visual inspection whether the threshold reliably generates a reliably distinguishes cells from noise.

Additional image filtering techniques, e.g., based on intensity smoothing, can be applied to the image. The noise filtering can avoid false "on" pixels and thus prevent creation of a new blob data record, e.g., if the size of the blob is sufficiently small. The noise filtering can also avoid false "off" pixels to improve the calculation of the total number of pixels in the second connected region.

Another implementation of identifying connected regions of pixels that have a minimum intensity is a maximally stable extremal regions (MSER) algorithm. In this technique, pixels in the digital image are sorted in intensity order. The sorted pixels are placed one-by-one to a blank image to grow blobs. In particular, the process includes a try-catch clause including a for-loop with sorted intensity index as the iteration variable. Inside this for loop, ending conditions are first checked to see if an image background intensity has been reached or not. The ending conditions can include two aspects: if the number of blobs in the image reaches 20, and if the largest blob in the image reaches a size of 3000 pixels. If, for the given iteration with the given pixel intensity at the given image position, the ending condition is not reached, that iteration will go through by placing that given pixel intensity at that given image position.

After the placement of a pixel, adjacent pixels are checked to see if there are already placed pixels present in the image or not. If there are, existing blob data records will be updated for this pixel's placement (e.g., the pixel is assigned to a blob that has already been noted), otherwise, a new blob data record will be created and stored (e.g., the pixel is assigned a new blob record). Such pixel placement will continue until the ending condition is reached. When the ending condition is reached, the iteration will stop, and the operation will exit for loop and the try-catch clause is completed. Maximally stable extremal regions are discussed in J. Matas et al., "Robust Wide Baseline Stereo from Maximally Stable Extremal Regions," Electronic Proceedings of The 13th British Machine Vision Conference (2002).

In some implementations, the digital image is divided into a plurality of regions, and each region is analyzed. The number of pixels for the regions can be selected such that the region can be larger than the expected size of the target cells, e.g., by about a factor of 3 to 10. For example, the digital image can be divided into rectangular regions that are, for example, 50 to 200 pixels on a side, e.g., into 100×100 pixel squares. Assuming that pixels are 0.648 μm on a side, this 100×100 pixel region can represent a 64.8 μm×64.8 μm area on the observation slide. Since CTCs measure between 8 μm to 20 μm, the region is large enough for the CTC to fit completely within the area.

In some implementations, if a connected region is identified as including more than a threshold number of pixels, a new re-centered region is selected that is centered on the connected region, and the identification of overlapping "blobs" is performed for the re-centered region. The re-centering can include forming an image that includes portions from multiple adjacent regions of a segmented image array.

Next, whether each first connected region overlaps a second region is determined (step 252a). Since a circulating tumor cell includes both a nucleus and cytoskeleton, presence of a connected region in one of the first or second color channels without a corresponding connected region in the other of the first and second color channels indicates that the connected region is not part of and therefore not a target cell and tagged as such. Thus, the computer 250 can determine regions of overlap of the "blobs" in the first color channel and the second color channel; if there is no overlap then a blob can be rejected as a candidate.

In some implementations, the second connected region can be considered to overlap the first connected region if the second region overlaps and/or fits within the first connected region. In some implementations, the first connected region is required to surround the second connected region, e.g., the first connected region forms a continuous annulus around the second connected region. Binary filtering of two of the channels, e.g., the blue and red channels, can be performed as a part of determining the overlap between blue blob and red blob.

The potential candidates indicated by overlapping connected regions from the first and second color channels can now be subjected to one or more shape tests.

A first shape test is to determine whether an aspect ratio of the overlapping connected falls within threshold aspect ratio range. The target cells, e.g., CTCs, are generally not elongated. Assuming the aspect ratio is the ratio of the shorter measurement to the longer measurement, then if the overlapping connected region has an aspect ratio below a threshold, this indicates that the overlapping connected regions is too elongated and is not a candidate.

Figure 6A:
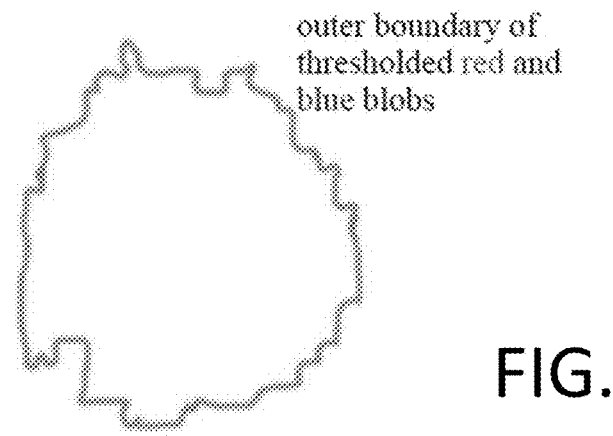
FIGS. 6A-6C illustrate a method of determining an aspect ratio.

In some implementations, to determine the aspect ratio, as shown in FIG. 6A, a combined region that is the union of the first connected region and the overlapping second connected region can be determined, and then the outer boundary of the combined region can be determined. The outer boundary can be the set of pixels on the outer perimeter of the combined region.

Figure 6B:
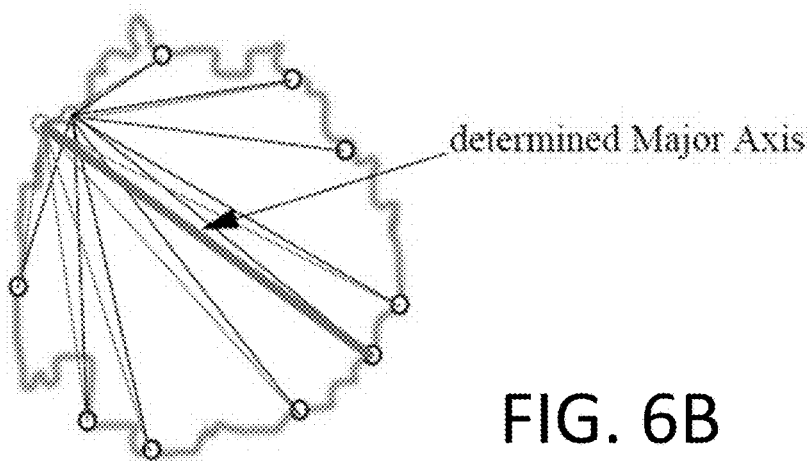

Next, as shown in FIG. 6B, a major axis for the combined region can be calculated. The major axis can be the line segment connecting the two pixels on the boundary that are farthest apart. For example, to determine the major axis, perform a function that for each pixel on the boundary, the distance between that pixel and each other pixel on the boundary can be determined; the pair with the greatest distance provide the two pixels that define the major axis.

Figure 6C:
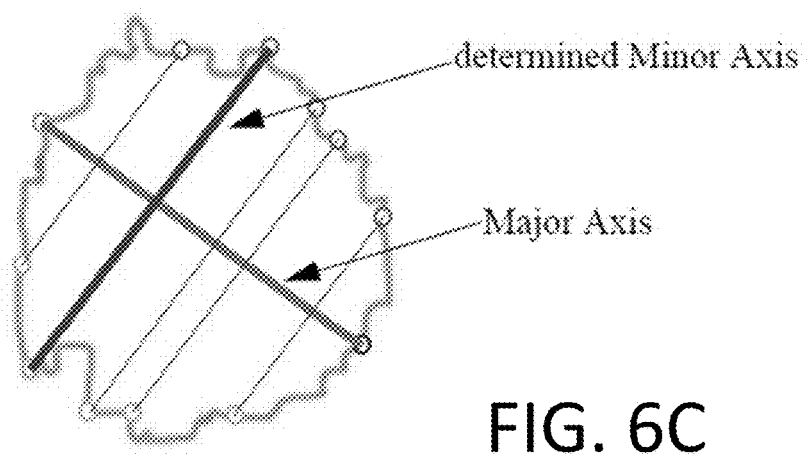

Then, as shown in FIG. 6C, the minor axis can be calculated for the combined region. The major axis splits the combined region into two halves. The minor axis can be the longest line segment that is perpendicular to the major axis that connects two pixels on the boundary on opposite sides of the major axis. For example, to determine the minor axis, for each pixel on the boundary on one side of the major axis, the distance between that pixel and the pixel on the boundary on the other side of the major axis on a line perpendicular to the major axis can be determined; the pair with the greatest distance provide the two pixels that define the minor axis.

The aspect ratio can be calculated as the ratio of the length of the minor axis to the length of the major axis. The aspect ratio can be compared to a threshold value. For example, if the aspect ratio is less than 0.4, e.g., less than 0.35, e.g., less than 0.3, then the overlapping connected region can be eliminated as a candidate cell.

A second shape test is to compare the fill factor of the overlapping connected regions. This provides an alternate way to detect an elongated region or to eliminate extreme irregularity in shape.

Figure 7:
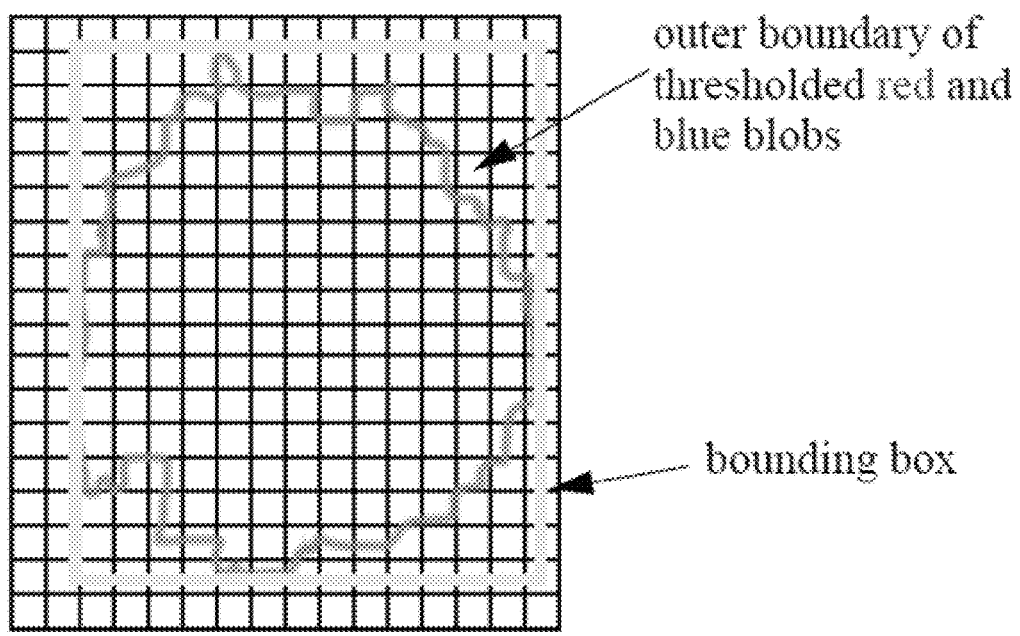
FIG. 7 illustrates a bounding box surrounding a "blob" in a digital image.

In some implementations, referring to FIG. 7, to determine the fill factor, a bounding box is established around the combined region. The bounding box is a rectangle with an upper and lower boundary that match the uppermost and lowermost pixels of the combined region, and a right and left boundary that match the rightmost and leftmost pixels of the combined region.

The number of pixels within the outer boundary of the combined region can be counted, and the number of pixels that are outside the combined region but inside the boundary box (also known as the "extent") can be counted. The ratio of the number of pixels within the outer boundary to the number of pixels in the extent is compared to a fill ratio threshold. If the ratio is less than the fill ratio threshold, the combined region is not a candidate. The fill ratio threshold can be about 0.4 to 0.85, e.g., 0.60.

Assuming that all of the prior tests are passed, the combined region can be identified as a candidate, although it is possible for non-target cells and white blood cells to pass these tests. Therefore, an additional process can be used to screen white blood cells. In general, this step includes determining an intensity ratio between two different channels in the combined region.

One of the channels can be the second channel. Another of the channels can be the third channel. In this case, a third connected regions in the third channel are determined, e.g., as described above for the first and second channels, and regions where the second connected regions and third connected regions overlap can be determined. The intensity values in the two channels in the region of overlap can be used to determine the intensity ratio. The spatially overlapping second connected regions and third connected regions for which the intensity ratio does not meet an intensity ratio can be eliminated as candidates.

In brief, a white blood cell should contain a greater amount of the third stain, and thus should show greater intensity in the third color channel. Thus, candidate regions that also show a strong intensity in the third color channel can be rejected.

In some implementations, this test can be performed by calculating an average intensity I2 of the second connected region. In addition, a third connected region of pixels of a minimum third intensity in the third color channel can be identified, e.g., using one of the techniques described above for the first and second connected regions. The average intensity I3 of the third connected region is also calculated.

In some implementations, the average background intensity within a color channel, e.g., the intensity within the extent region or within a selected image subregion that includes the combined area, is calculated. This average background intensity for the color channel is subtracted from the average intensity of the connected region in the channel to provide an adjusted average intensity.

The following formula can be used to determine whether the cell is a candidate cell, e.g., a CTC (Group 1), ambiguous (Group 2), or a white blood cell (Group 3).

$$\text{Group 1: } \frac{I2}{I2-I3} \leq 2$$

$$\text{Group 2: } \frac{I2}{I2-I3} > 2 \text{ and } \frac{I2}{I3} > 1$$

$$\text{Group 3: } \frac{I2}{I3} < 1$$

where I2 and I3 are the averages or adjusted averages discussed above.

The combined regions corresponding to Group 3 can be rejected; those regions that satisfy I2/I3≥2 can be marked as candidates for evaluation by the technician.

In review, using algorithms described herein, the computer 250 determines overlapping first connected regions and second connected regions from first and second color channels in the digital image. An aspect ratio of the spatially overlapping first connected regions and second connected regions is then determined based on one or more color channels. One or more spatially overlapping first connected regions and second connected regions for which the aspect ratio meets a threshold are then determined. Portions of the image corresponding to an identified spatially overlapping first connected region and second connected region are then displayed to an operator as candidates for classification.

Figure 8:
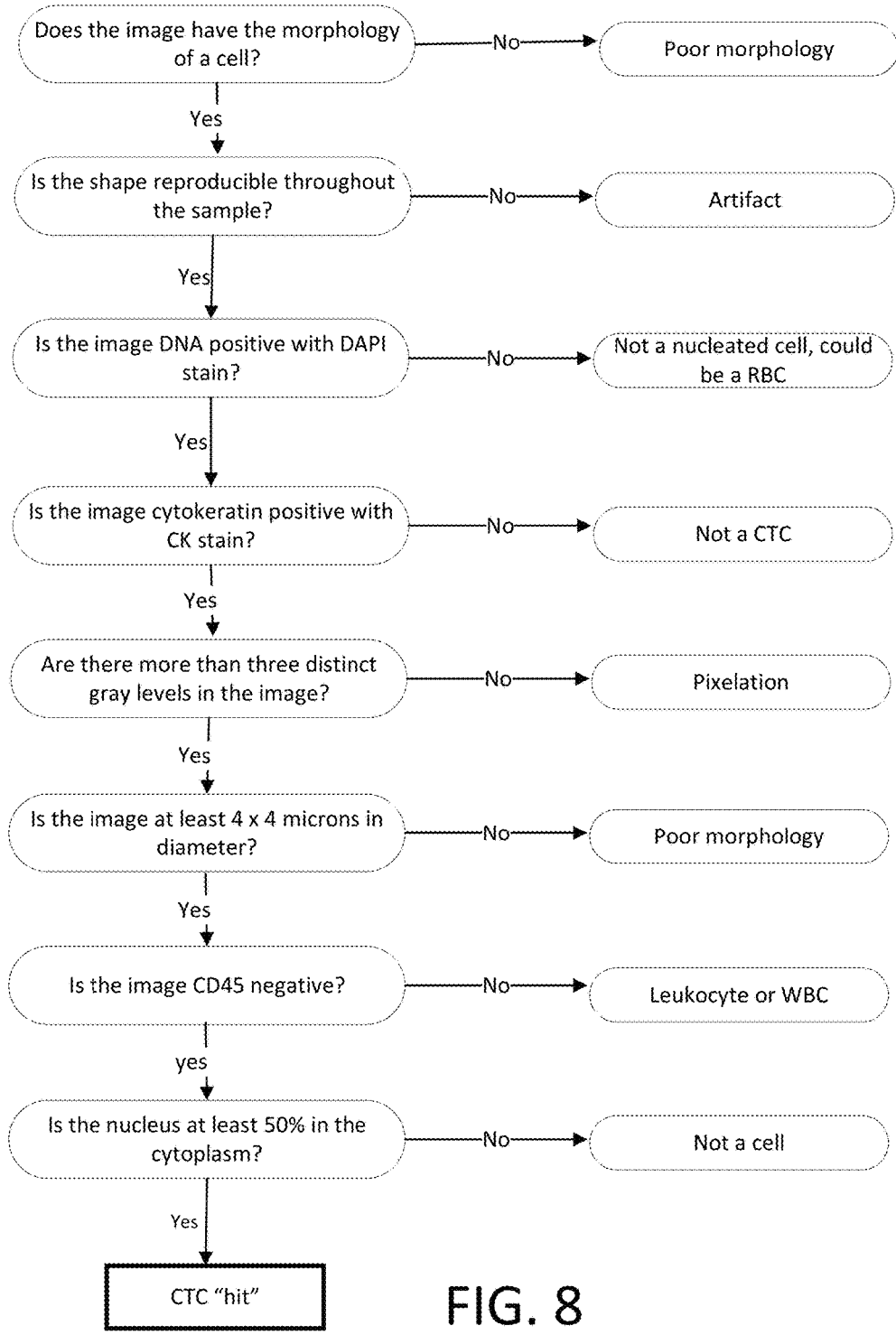
FIG. 8 is a flow chart illustrating considerations in determining whether an object in an image should be classified as a candidate.

FIG. 8 is a flow chart illustrating considerations in determining whether an object in an image should be classified as a candidate. This flow chart is not necessarily in the same order as the operations by software on computer 250.

Examples

Detection of CTCs finds important application in diagnosis and prognosis of cancer. The presence in peripheral blood of CTCs expressing on their surface the 'Epithelial Cell Adhesion Molecule' (EpCAM, a pan-epithelial (all-inclusive) differentiation antigen that is expressed on almost all carcinomas) is associated with decreased progression free survival and decreased overall survival in patients treated for metastatic breast cancer. CTCs that express EpCAM are abbreviated as "EpCAM+CTCs." For some platforms, an EpCAM+CTC count of 5 or more per roughly 7.5 ml of blood is predictive of shorter progression free survival and overall survival.

In another application, 2 to 10 mL of blood may be processed per sample, and the number of circulating tumor cells identified may be used to predict the risk or recurrence of diseases. In yet another implementation, the number of CTCs identified from the blood may be just one of several variables in a regression equation which contain other risk factors, other than CTCs, as variables.

In some implementations, a CTC should stain positive for CK-ALEXA568® (a red dye), be round, oval or polygonal with an intact membrane and at least 4 μm in size. A CTC should not stain positive for CD45-ALEXA488® (a green dye), as this stain recognizes an antigen present on leukocytes, and CTC cannot be white blood cells. A CTC should also stain positive for the DAPI nuclear stain (a blue dye), indicating that the nucleus is contained within the cytoplasm and smaller than the cytoplasm by at least 30%. The presence of a nucleus indicates that the cell is not a red blood cell, which is a-nuclear.

CTCs are shed by tumor masses into the bloodstream. Tracking and enumerating CTCs in peripheral blood early can alter treatment regimens and possibly slow metastasis. CTCs are rare and difficult to classify among other cells. As shown in FIG. 6, a field view of schematic cells derived from peripheral blood are stained before optical viewing. Image galleries of cells are presented for review, where each gallery contains a CK-ALEXA568® (cytokeratin) column, a DAPI nuclear counterstain, and a CD45-ALEXA488® stain for WBC (or other non-target cells), for example. A technologist can review each line and select those cells that qualify as tumor cells according to specific criteria. In some implementations, a technologist may interpret objects in image galleries as circulating tumor cells (CTCs), leukocytes (WBC), squamous cells, tumor cells with leukocytes in the same frame, non-target cells or dual positive cells, for example. Miscellaneous considerations when viewing image objects include a-nucleated cells, pixilated cells, detached nuclei and non-cellular debris such as artifacts and computer noise.

Using a light control, a first image is first captured with red light, a second image is captured with blue light and a third image is captured using green light.

The microscope may have a motorized platform capable of scanning the sample on the slide and capturing images in sections. Using automated steps, a computer-implemented process described herein interprets overlapping colors and shapes (circular/oval versus non-cellular). In certain implementations, the motorized platform reorients the slide and resolves which sections have CTCs. It stores these images as sections of interest for review.

Large, atypical appearing cells should not be counted as CTCs. Pixilated, blurry and non-intact cells should not be counted as CTCs. Rare contaminants may appear due to over-amplification of the CK-ALEXA568® or DAPI signals. These images do not meet the criteria for a CTC.

In one implementation, an image capture apparatus (e.g., a microscope) identifies first connected regions of blue pixels of a minimum first intensity. The connected blue pixels of a minimum first intensity correspond to putative WBC or CTC nuclei. Identification of connected regions of blue pixels is performed in 100×100 pixel patches. Once identified, the system will re-center the patch such that the connected regions of blue pixels are centered within the 100×100 pixel patch.

The image capture apparatus then identifies second connected regions of red pixels of a minimum second intensity. First connected regions of blue pixels and second connected regions of red pixels that spatially overlap are identified and an aspect ratio of the spatially overlapping first and second connected regions is determined. One or more spatially overlapping regions for which the aspect ratio meets a threshold, the region is then identified. Portions of the image corresponding to spatially overlapping first connected regions and second connected regions are then displayed to an operator as candidates for classification.

Definitions

The term "circulating tumor cells" (CTCs) is used herein to indicate nucleated cells in a circulating fluid (preferably peripheral blood) that are not leukocytes.

CTCs are rare cells that have left a primary tumor to enter the blood stream or lymphatic system. In the case of bladder cancer, CTCs can dislodge from a tumor mass and enter urine. In the case of salivary gland cancer, CTCs can detach from a tumor mass and enter saliva. Thus, the methods and processes described herein define a CTC as an object that has a nucleus (e.g., stains positive for DAPI), has epithelial cell features (e.g., stains positive for cytokeratin), and is not a leukocyte (e.g., does not stain positive for CD45). The object must be larger than 4×4 $\mu m^2$ and have cell-like morphology.

As used herein, the term "DAPI" refers to 4', 6-diamidino-2-phenylindole, a stain with fluorescent blue emission spectra that binds strongly to A-T rich regions in DNA. When used in fluorescence microscopy, DAPI passes through intact cell membranes in both live and fixed cells, thus capable of marking and differentiating between nucleated and a-nucleated cells such as red blood cells.

As used herein, the term "CK" refers to cytokeratin, which is a keratin-containing intermediate filament found in the intracytoplasmic cytoskeleton of epithelial cells. The term "anti-CK/ALEXA568®" refers to monoclonal antibodies specific for cytokeratin that are conjugated to ALEXA568®, an organic dye with fluorescent red emission spectra, thus capable of marking and differentiating epithelial cells. Note the anti-CK/ALEXA568® can also refer to a combination of a first antibody recognizing CK and a second antibody conjugated to a dye such as ALEXA568® that targets the first antibody. Anti-cytokeratins (CKs) can be anti-pan (all-inclusive) cytokeratin or anti-individual cytokeratin isotypes (e.g., cytokeratin 1 to cytokeratin 20) or a combination of any number of cytokeratin isotypes. More generally, "anti-CK/PE" and "anti-CK/APC" refer to monoclonal antibodies specific for cytokeratin that are conjugated to classes of organic dyes with fluorescent red emission spectra, such as, allophycocyanin (APC) and phycoerythrin (PE), for example.

As used herein, the term "CD45" refers to cluster differentiation 45, an antigen present on the surface of leukocytes. Anti-CD45-ALEXA488® is a monoclonal antibody specific for CD45 conjugated to ALEXA488®, an organic dye with fluorescent green emission spectra, thus capable of marking and differentiating leukocytes, also referred to as white blood cells (WBC). Note the anti-CD45/ALEXA488® can also refer to a combination of a first (CD45) and a second antibody (ALEXA488®) that targets the first antibody.

As used herein, the term "bodily fluid" includes ascites, saliva, urine, synovial fluid, peritoneal fluid, amniotic fluid, cerebrospinal fluid, serosal fluid and/or spinal fluid.

The term "nuclear stain" refers to a dye compound used to indicate the presence of a nucleus in a cell. Nuclear stains include such intercalating dyes such as acridine orange, ethidium bromide, ethidium monoazide, Hoechst dyes, propidium iodide and DAPI.

The term "fluorescent label", as used herein, refers to a fluorophore that can be covalently attached to another molecule, such as a protein or nucleic acid, which attachment is generally accomplished by using a reactive derivative of the fluorophore that selectively binds to a functional group contained in the target molecule. Fluorescent labels include, but are not limited to allophycocyanin (APC), fluoresceins (FITC), rhodamines (FAM, R6G, TET, TAMRA, JOE, HEX, CAL Red, VIC, and ROX), Texas red, BODIPY, coumarins, cyanine dyes (thiazole orange [TO], oxazole yellow [YO], TOTO, YOYO; Cy3, Cy5), ALEXA FLUOR® dyes, DYLIGHT® dyes Green Fluorescent Protein (GFP), and phycoerythrin (PE).

The term "biological sample" as used herein, is used in its broadest sense as containing nucleic acids or the protein translation products thereof. A sample may comprise a bodily fluid such as blood; the soluble fraction of a cell preparation, or an aliquot of media in which cells were grown; a chromosome, an organelle, or membrane isolated or extracted from a cell; genomic DNA, RNA, or cDNA in solution or bound to a substrate; a cell; a tissue; a tissue print; a fingerprint; cells; skin, and the like. In preferred implementations, the term refers to biological material obtained from a subject that contains cells and encompasses any material in which CTCs can be detected. A sample can be, for example, whole blood, plasma, saliva or other bodily fluid or tissue that contains cells. A preferred sample is whole blood, more preferably peripheral blood, still more preferably a peripheral blood cell fraction, still more preferably CTCs isolated or enriched from blood.

The term "antibody" as used herein refers to any of a large variety of proteins normally present in the body or produced in response to an antigen which it neutralizes, thus producing an immune response. An antibody preferably comprises immunoglobulins of the IgG subtype.

The term "reacts specifically with" as used herein, refers to the binding between an antibody and an antigen with a specificity (and generally also affinity) which is better than the binding between the same antigen and a non-specific antibody.

A volume of blood (or other bodily secretion) necessary for analysis using the systems and methods described herein may be equal to about or less than 25 µL, 50 µL, 75 µL, 100 µL, 0.2 mL, 0.5 mL, 1 mL, 1.5 mL, 2 mL, 2.5 mL, 3 mL, 3.5 mL, 4 mL, 4.5 mL, 5 mL, 5.5 mL, 6 mL, 6.5 mL, 7 mL, 7.5 mL or 8 mL, 9 mL, 10 mL, 11 mL, 12 mL, 13 mL, 14 mL, 15 mL or 16 mL. The volume of blood necessary for analysis using the systems and methods described herein may be equal to or up to 25 µL, 50 µL, 75 µL, 100 µL, 0.2 mL, 0.5 mL, 1 mL, 1.5 mL, 2 mL, 2.5 mL, 3 mL, 3.5 mL, 4 mL, 4.5 mL, 5 mL, 5.5 mL, 6 mL, 6.5 mL, 7 mL, 7.5 mL or 8 mL, 9 mL, 10 mL, 11 mL, 12 mL, 13 mL, 14 mL, 15 mL or 16 mL. As used herein, the term "about" may refer to an amount within +/−1, 2, 3, 4, 5, 6, 7, 8, 9, or 10% of a subsequently mentioned value.

For example, a sample of 11 mL of blood may also be referred to as a sample of blood equal to about 10 mL. Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention. The following examples are presented in order to more fully illustrate the preferred implementations of the invention. They should in no way be construed, however, as limiting the broad scope of the invention.

Computer Systems

One or more of the computers described above, e.g., the computer 250, include a processor 252, a memory 254, a storage device 256, and one or more input/output interface devices 258. Each of the components 252, 254, 256, and 258 can be interconnected, for example, using a system bus 259.

The processor 252 is capable of processing instructions for execution within the system 250. The term "execution" as used here refers to a technique in which program code causes a processor to carry out one or more processor instructions. In some implementations, the processor 252 is a single-threaded processor. In some implementations, the processor 252 is a multi-threaded processor. In some implementations, the processor 252 is a quantum computer. The processor 252 is capable of processing instructions stored in the memory 254 or on the storage device 256.

The memory 254 stores information within the system 250. In some implementations, the memory 254 is a computer-readable medium. In some implementations, the memory 254 is a volatile memory unit. In some implementations, the memory 254 is a non-volatile memory unit.

The storage device 256 is capable of providing mass storage for the system 250. In some implementations, the storage device 256 is a non-transitory computer-readable medium. In various different implementations, the storage device 254 can include, for example, a hard disk device, an optical disk device, a solid-state drive, a flash drive, magnetic tape, or some other large capacity storage device. In some implementations, the storage device 254 may be a cloud storage device, e.g., a logical storage device including one or more physical storage devices distributed on a network and accessed using a network, such as the network 260 shown in FIG. 3. In some examples, the storage device 256 may store long-term data, such as the digital images.

The input/output interface devices 258 provide input/output operations for the system 250. In some implementations, the input/output interface devices 256 can include one or more of a network of interface devices, e.g., an Ethernet interface, a serial communication device, e.g., an RS-232 interface, and/or a wireless interface device, e.g., an 802.11 interface, a 3G wireless modem, a 4G wireless modem, etc. A network interface device allows the system 256 to communicate, for example, transmit and receive data such as the digital images, e.g., using the network 260. In some implementations, the input/output device can include driver devices configured to receive input data and send output data to other input/output devices, e.g., keyboard, printer and display devices. In some implementations, mobile computing devices, mobile communication devices, and other devices can be used.

The software to carry out the image analysis and other operations of the system 200 can be realized by instructions that upon execution cause one or more processing devices to carry out the processes and functions described above. Such instructions can include, for example, interpreted instructions such as script instructions, or executable code, or other instructions stored in a computer readable medium.

Although an example processing system has been described, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification, such as storing, maintaining, and displaying artifacts can be implemented as one or more computer program products, i.e., one or more modules of computer program instructions encoded on a tangible program carrier, for example a computer-readable medium, for execution by, or to control the operation of, a processing system. The computer readable medium can be a machine readable storage device, a machine readable storage substrate, a memory device, or a combination of one or more of them.

The term "system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM, DVD-ROM, and Blu-Ray disks. The processor and the memory can be supplemented by, or incorporated in, special purpose logic circuitry. Sometimes a server is a general purpose computer, and sometimes it is a custom-tailored special purpose electronic device, and sometimes it is a combination of these things. Implementations can include a back end component, e.g., a data server, or a middleware component, e.g., an application server, or a front end component, e.g., a client computer having a graphical user interface or a Web browser through which a user can interact with an implementation of the subject matter described is this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

Although the discussion above has focused on detection of CTCs that are epithelial cells, in principle the techniques described herein could be applied to other kinds of cells, such as, for example, other circulating rare cells (CRCs), disseminated cancer cells, stem cells (e.g., tumor stem cells and bone marrow stem cells), fetal cells, bacteria, endothelial cells or the like.

A number of implementations have been described. Nevertheless, it will be understood that various modifications may be made without departing from the spirit and scope of the disclosure. Accordingly, other implementations are within the scope of the following claims.

What is claimed is:

1. A method for identifying candidate target cells within a biological fluid specimen, comprising:
    obtaining a biological fluid specimen;
    preparing the biological fluid specimen by staining cell nuclei in the biological fluid specimen with a first bio-conjugated dye having a first color and configured to bind nucleic acids in the cell nuclei of the target cells, and staining cytoskeletal cell features in the biological fluid specimen with a second bio-conjugated dye having a second color and configured to bind to cytoskeletal cell features of the target cells, and staining white blood cells in the biological fluid specimen with a third bio-conjugated dye having a third color and configured to bind to human leukocyte antigens in the biological fluid specimen;
    capturing a digital image of the biological fluid specimen, the digital image having a plurality of color channels; and
    applying image analysis to the digital image including
        receiving the digital image in a computer,
        identifying, in the computer, first connected regions of pixels of a minimum first intensity in a first channel of the plurality of color channels,
        identifying, in the computer, second connected regions of pixels of a minimum second intensity in a second channel of the plurality of color channels,
        determining, in the computer, first connected regions and second connected regions that spatially overlap,
        determining, in the computer, an aspect ratio of the spatially overlapping first connected regions and second connected regions based on a color channel of the plurality of color channels,
        identifying, in the computer, first connected regions and second connected regions that spatially overlap and for which the aspect ratio meets an aspect ratio threshold;
        determining, in the computer, a second connected region and a third connected region that spatially overlap,
        determining, in the computer, an intensity ratio of the spatially overlapping second connected region and third connected region based on two color channels of the plurality of color channels,
        eliminating as a candidate, in the computer, a spatially overlapping first connected region and second connected region corresponding to a spatially overlapping second connected region and third connected region for which the intensity ratio does not meet an intensity ratio threshold, and
        providing a portion of the image corresponding to a remaining identified spatially overlapping first connected region and second connected region to a classifier as candidates for classification.

2. The method of claim 1, wherein the first color is blue, the second color is red or orange, and the third color is green.

3. The method of claim 1, wherein
    the first bio-conjugated dye includes DAPI (4',6-diamidino-2-phenylindol),
    the second bio-conjugated dye includes a red or orange fluorescent dye conjugated to an anti-cytokeratin (CK) antibody, and
    the third bio-conjugated dye includes a green fluorescent dye conjugated to an anti-CD45 antibody, or a combination of a first antibody, anti-CD45, and a second antibody pre-conjugated to a green fluorescent dye and targeting CD45.

4. The method of claim 1, wherein
    the second bio-conjugated dye includes a red or orange fluorescent dye conjugated to an anti-cytokeratin (CK) antibody, or a combination of a first antibody, anti-CK, and a second antibody pre-conjugated to a red or orange fluorescent dye and targeting CK.

5. A computer program product for identifying candidate target cells within a biological fluid specimen, the computer program product tangibly embodied in a non-transitory computer readable medium, comprising instructions to cause a processor to
    receive a digital image of the biological fluid specimen, the digital image having a plurality of color channels,
    identify first connected regions of pixels of a minimum first intensity in a first channel of the plurality of color channels,
    identify second connected regions of pixels of a minimum second intensity in a second channel of the plurality of color channels,
    determine first connected regions and second connected regions that spatially overlap,
    determine an aspect ratio of the spatially overlapping first connected regions and second connected regions based on a color channel of the plurality of color channels,
    identify a spatially overlapping first connected regions and second connected regions for which the aspect ratio meets an aspect ratio threshold;
    determine a second connected region and a third connected region that spatially overlap,
    determine an intensity ratio of the spatially overlapping second connected region and third connected region based on two color channels of the plurality of color channels, eliminate as a candidate a spatially overlapping first connected region and second connected region corresponding to a spatially overlapping second connected region and third connected region for which the intensity ratio does not meet an intensity ratio threshold, and provide a portion of the image corresponding to a remaining identified spatially overlapping first connected region and second connected region to a classifier as a candidate for classification.

6. The computer program product of claim 5, wherein the instructions to identify the first connected regions comprise instructions to identifying first connected regions that have a minimum first size, and wherein the instructions to identify the second connected regions comprise instructions to identify second connected regions that have a minimum second size.

7. The computer program product of claim 6, wherein the instructions to identify the first connected regions comprise instructions to identify first connected regions that have a maximum first size, and wherein the instructions to identify the second connected regions comprise instructions to identify second connected regions that have a maximum second size.

8. The computer program product of claim 6, wherein the instructions to identify the first connected regions and the instructions to identify the second connected regions comprises a maximally stable extremal regions (MSER) algorithm.

9. The computer program product of claim 6, wherein the instructions to identify the first connected regions comprise instructions to divide the digital image into a plurality of portions, search each portion for a potential first connected region, and identify a new portion of the digital image centered on a potential first connected region found from the search.

10. The computer program product of claim 6, wherein the instructions to determine first connected regions and second connected regions that spatially overlap comprise instructions to determine whether a boundary of a second connected region fits inside or overlies a boundary of the first connected region.

11. The computer program product of claim 6, comprising instructions to determine a combination of the first connected region and the second connected region.

12. The computer program product of claim 11, wherein the instructions to determine the aspect ratio comprise instructions to find a major axis that extends between two points that are farthest apart on a boundary of the combination, find a minor axis that extends perpendicular to the major axis and between two points that are farthest apart on the boundary on opposites sides of the major axis, and calculate a ratio of the minor axis to the major axis.

13. The computer program product of claim 12, wherein the aspect ratio threshold is 0.4 or less.

14. The computer program product of claim 11, further comprising instructions to determine a boundary box around the combination, determine a first number of pixels within a boundary of the combination and a second number of pixels in an extent, determine a ratio of the first number of pixels to the second number of pixels, and compare the ratio to an extent threshold.

15. The computer program product of claim 14, wherein the extent threshold is between 0.4 and 0.85.

16. The computer program product of claim 11, wherein the combination is a union of the first connected region and the second connected region.

17. The computer program product of claim 5, wherein the instructions to determine the intensity ratio comprise instructions to determine a first average intensity of the second connected region, determine a second average intensity of the third connected region, and determine a ratio of the first average intensity to the second average intensity.

18. The computer program product of claim 17, wherein the spatially overlapping second connected region and third connected region is eliminated if the ratio is below the threshold.

19. The computer program product of claim 18, wherein the spatially overlapping second connected region and third connected region is eliminated if $$\frac{I2}{I3} < 1$$

where I2 is the first average intensity and I3 is the second average intensity.

20. The computer program product of claim 5, wherein the first color is blue, the second color is red or orange, and the third color is green.

21. A method for enumerating a target cell population within a biological fluid specimen, comprising:
obtaining a biological fluid specimen;
preparing the biological fluid specimen by staining cell nuclei in the biological fluid specimen with a first bio-conjugated dye having a first color and configured to bind nucleic acids in the cell nuclei of the target cells and staining cytoskeletal cell features in the biological fluid specimen with a second bio-conjugated dye having a second color and configured to bind to cytoskeletal cell features of the target cells and staining non-target cells in the biological fluid specimen with a third bio-conjugated dye having a third color and configured to bind to human leukocyte antigens in the biological fluid specimen;
capturing a digital image of the biological fluid specimen, the digital image having a plurality of color channels and at least two color channels; and
applying an image analysis to the digital image including
receiving the digital image in a computer,
identifying, in the computer, first connected regions of pixels of a minimum first intensity in a first channel of the plurality of color channels,
identifying, in the computer, second connected regions of pixels of a minimum second intensity in a second channel of the plurality of color channels,
identifying, in the computer, second connected regions of pixels of a minimum second intensity in a second channel of the plurality of color channels,
determining, in the computer, first connected regions and second connected regions that spatially overlap,
determining, in the computer, an aspect ratio of the spatially overlapping first connected regions and second connected regions based on two color channels of the plurality of color channels,
identifying, in the computer, spatially overlapping first connected regions and second connected regions for which the aspect ratio meets an aspect ratio threshold; and
determining, in the computer, a second connected region and a third connected region that spatially overlap, determining, in the computer, an intensity ratio of the spatially overlapping second connected region and third connected region based on two color channels of the plurality of color channels, and eliminating as a candidate, in the computer, a spatially overlapping first connected region and second connected region corresponding to a spatially overlapping second connected region and third connected region for which the intensity ratio does not meet an intensity ratio threshold;

classifying a candidate as a target cell or a non-target element based on a portion of the image corresponding to a remaining identified spatially overlapping first connected region and second connected region; and counting any candidate classified as a target cell, to generate a count value.

22. A method for determining likelihood of cancer in a human subject, comprising:

comparing the count value obtained according to claim 21 with a statistically determined count of circulating epithelial cells from a group of tumor-free patient controls; and assigning a likelihood of cancer occurrence when the total count exceeds a pre-determined value based on statistical averages of circulating epithelial cell counts from healthy subjects compared with statistical averages of circulating epithelial cell counts from cancer patients.

\* \* \* \* \*

UNITED STATES PATENT AND TRADEMARK OFFICE
CERTIFICATE OF CORRECTION

PATENT NO. : 9,738,937 B1  
APPLICATION NO. : 15/476848  
DATED : August 22, 2017  
INVENTOR(S) : Huangpin B. Hsieh et al.

Page 1 of 1

It is certified that error appears in the above-identified patent and that said Letters Patent is hereby corrected as shown below:

Column 22, Lines 25-26, Claim 3: please delete "(4' ,6-diamidino-2-phenylindol)," and insert therefor -- (4',6-diamidino-2-phenylindole, --; and Column 23, Line 52, Claim 12: please delete "opposites sides" and insert therefor -- opposite sides --.

Signed and Sealed this  
Twenty-sixth Day of June, 2018

Andrei Iancu  
*Director of the United States Patent and Trademark Office*